United States Patent
Danielsson et al.

(10) Patent No.: US 6,726,642 B2
(45) Date of Patent: Apr. 27, 2004

(54) DEVICE FOR COMPRESSION OF THE LOWER EXTREMITIES FOR MEDICAL IMAGING PURPOSES

(76) Inventors: Barbro Danielsson, Almvagen 28, 437 40 Lindhome (SE); Thomas Nicklasson, Kuttervagen 39, 439 35 Onsala (SE); Jan A. G. Willen, Krikonvagen 19, 435 43 Molnlycke (SE)

(*) Notice: Subject to any disclaimer, the term of this patent is extended or adjusted under 35 U.S.C. 154(b) by 0 days.

(21) Appl. No.: 10/160,723

(22) Filed: Jun. 3, 2002

(65) Prior Publication Data

US 2002/0193683 A1 Dec. 19, 2002

Related U.S. Application Data

(63) Continuation of application No. PCT/SE00/02629, filed on Dec. 20, 2000.

(30) Foreign Application Priority Data

Dec. 20, 1999 (SE) ............................................ 9904662

(51) Int. Cl.[7] .................................................. A61F 5/00
(52) U.S. Cl. ............................... 602/5; 602/23; 602/32
(58) Field of Search .............................. 128/845, 846, 128/886, 882; 602/5, 16, 23, 26, 32, 33, 35, 40

(56) References Cited

U.S. PATENT DOCUMENTS

| | | | |
|---|---|---|---|
| 158,894 A | * 1/1875 | Bissell | |
| 1,089,801 A | * 3/1914 | Swanson | |
| 3,629,581 A | 12/1971 | Smith | |
| 4,202,355 A | 5/1980 | Loeffler | |
| 4,320,749 A | 3/1982 | Highley | |
| 4,407,277 A | 10/1983 | Ellison | |
| 4,911,152 A | * 3/1990 | Barnes | |
| 5,273,520 A | * 12/1993 | Rebmann | 602/5 |
| 5,541,515 A | 7/1996 | Tsujita | |
| 5,562,094 A | 10/1996 | Bonutti | |
| 5,810,006 A | 9/1998 | Votruba et al. | |
| 5,827,209 A | * 10/1998 | Gross | 602/19 |

* cited by examiner

Primary Examiner—Michael A. Brown
(74) Attorney, Agent, or Firm—Gauthier & Connors LLP

(57) ABSTRACT

The present invention relates to a device for compression of the lower extremities for medical imaging purposes, in particular for diagnostic purposes at complementary examination using computed tomography (CT) or magnetic resonance tomography (MRT) wherein the device comprises a waist arrangement to be placed around and in firm contact with the hip region of a patient, a knee arrangement to be placed in the vicinity of and in firm contact with the knee of a patient, a foot plate comprising pressure sensors and being arranged to accommodate a foot or the feet of a patient, whereby said sensors are arranged to monitor the pressure of the respective foot on said foot plate, strings connecting said waist arrangement and said foot plate arrangement, which strings can be stretched independently of each other and comprise each a tension meter to monitor the force by which the strings are strained.

6 Claims, 1 Drawing Sheet

DEVICE FOR COMPRESSION OF THE LOWER EXTREMITIES FOR MEDICAL IMAGING PURPOSES

Figure 1:
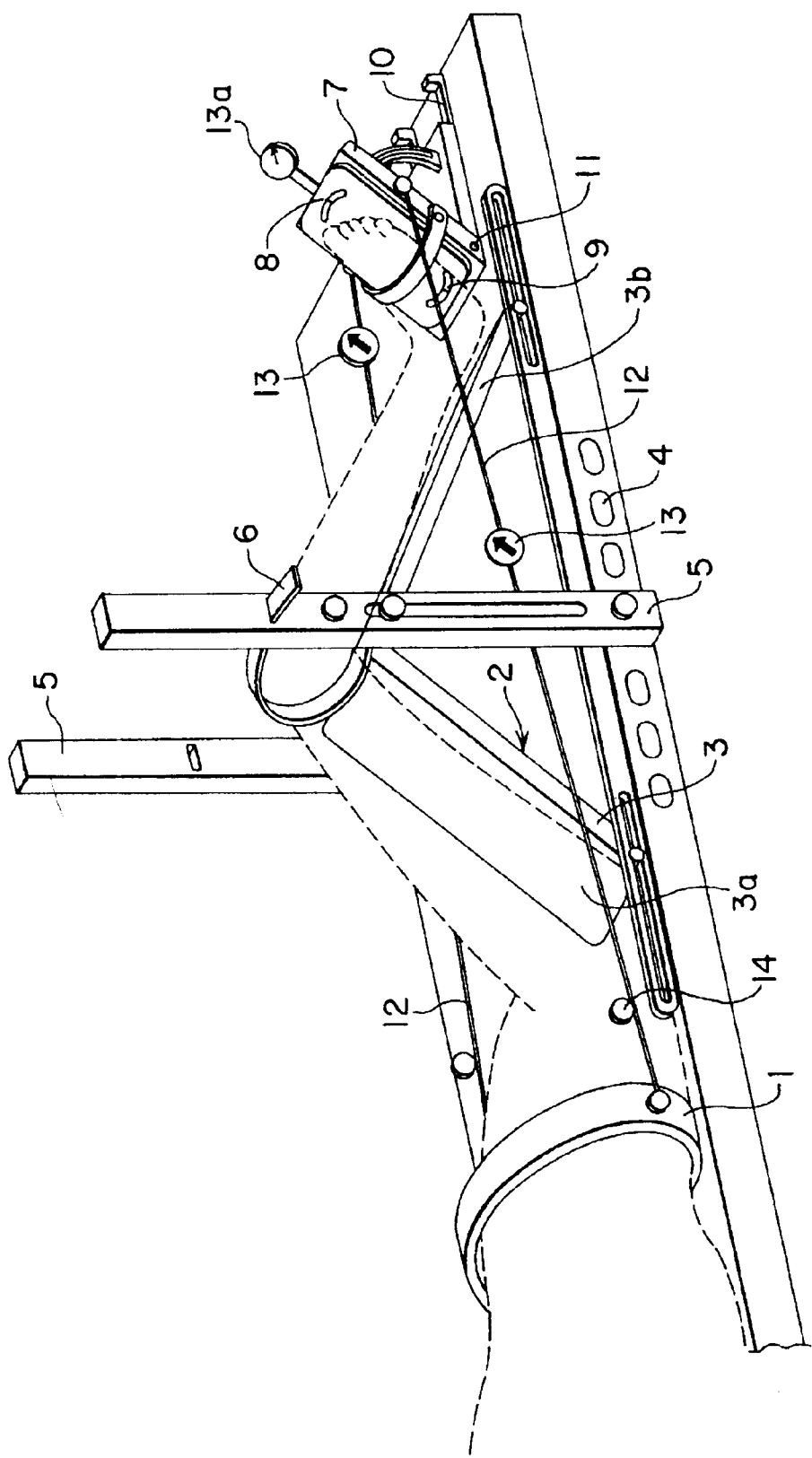

This is a continuation of application Ser. No. PCT/SE00/02629, filed Dec. 20, 2000.

TECHNICAL FIELD

The present invention relates to a device for compression of the lower extremities for medical imaging purposes, in particular for diagnostic purposes at complementary examination using computed tomography (CT) or magnetic resonance tomography (MRT).

The object of the present invention is to obtain a device the use of which provides an aid for an adequate and reproducible examination of the lower extremities under load in connection with computed tomography and/or magnetic resonance tomography, in particular for the diagnosis of development of arthrosis, changes of cartilage in beginning arthrosis, luxation, sacroiliac joint changes with regard to the hip joint; diagnosis of cruciate ligaments and meniscus damages, development of cartilage, patellar luxation, subluxations, preconditions for meniscus transplantations in the knee; diagnosis of cartilage damages, changes of tendons, luxations, and osteochondritis in the ankle.

BACKGROUND OF THE INVENTION

Diagnosis of the lower extremities with regard to development of arthrosis, changes of cartilage in beginning arthrosis, luxation, sacroiliac joint changes with regard to the hip joint, diagnosis of cruciate ligaments and meniscus damages, development of cartilage, patellar luxation, subluxations, preconditions for meniscus transplantations in the knee; diagnosis of cartilage damages, changes of tendons, luxations, and osteochondritis in the ankle are hard to carry out under well-defined conditions and the market does not recognise any such diagnostic tools or equipment for said purpose.

EP 95920357.1 discloses a device for compression of the lumbar spine for medical imaging purposes, and then in particular for the diagnosis of the spinal cord canal and nerve structures (spinal stenosis) present.

Further, it is previously known from U.S. Pat. No. 3,629,581 a device for positioning a patients shoulders in connection on with an X-ray examination of the spine of a patient, whereby the upper spinal column is pressed downwards towards the examination table and makes it possible to obtain good X-ray pictures of the upper vertebras. Hereby a pressure is applied over the spinal column of the lying patient via two flexible strings provided with handles for the patient which strings are arranged around a foot plate.

U.S. Pat. No. 4,202,355 discloses an X-ray grid orthometer used for measuring the leg length of individuals that may have an anatomical leg length imbalance, where the device composes a fame means mountable on a support for adjusting to the length of the legs of a patient, whereby the frame comprises two foot plates onto which the patient's feet are placed. Further the X-ray grid orthometer comprises a pair of pulleys and a flexible elongated member arranged as to be engageable at the end portion by a patient for compressing the lumbar spine and legs the patient pulling with both hands on the flexible member.

There is thus a problem to be solved, viz. to obtain an apparatus or device for the diagnosis of development of arthrosis, changes of cartilage in berg arthrosis, luxation, sacroiliac joint changes with regard to the hip joint; diagnosis of cruciate ligaments and meniscus damages, development of cartilage, patellar luxation, subluxations, preconditions for meniscus transplantations in the knee; diagnosis of cartilage damages, changes of tendons, luxations, and osteochondritis in the ankle under well-defined conditions.

DESCRIPTION OF THE PRESENT INVENTION

It has now surprisingly been shown possible to be able to solve this problem by the present invention which is characterized in that the device comprises a waist arrangement to be placed around and in film contact with the hip region of a patient, a knee arrangement to be placed in the vicinity of and in firm contact with the knee of a patient, a foot plate comprising pressure sensors and being arranged to accommodate the feet of a patient, whereby said sensors are arranged to monitor the pressure of the respective foot on said foot plate, strings connecting said waist arrangement and said foot plate arrangement, which strings can be stretched independently of each other and comprise each a tension meter to monitor the force by which the strings are strained.

By means of the present invention a controlled load of the lower extremities can be obtained when the waist arrangement applied around a patient's hip region and the knee arrangement is placed in the vicinity of the knee and the strings are stretched to a certain load between the waist arrangement and the foot plate. Further, the load can be applied asymmetric as well whereby a single knee can be examined and diagnosed in any bent and luxated position. Thus a knee can be examined during load at different degrees of flexion and rotation or both, examined when bent at different angles, optionally at fixation of the knee at three dimensions. The diagnosis and examination is further facilitated as the foot plate in one particular embodiment is made rotatable with regard to foot blade and heel, or both.

The invention will now be described more in detail with reference to the attached drawing, showing a preferred device of the invention, however, without being restricted thereto, wherein FIG. 1 shows a perspective view of one embodiment of a device according to the present invention.

1 denotes a waist arrangement which is arranged to be placed around the waist and immediately in connection with the hip region of a patient and thereby resting on the hipbones (innominate bones), whereby it is fastened conveniently using cords of the burdock type. The waist arrangement is applied firmly but still comfortably, but in such a manner that it does not slide over the body/hipbones (innominate bones).

A knee/leg arrangement 2 is provided with means to have it arranged firmly and non-slidable to a knee. The knee/leg arrangement 2 is comprises a resting plate 3 for the thigh and the lower part of the leg of a patient, which resting plate 3 can be raised to an upright inclined position, whereby it is preferably adjustable as to its length to fit any thigh length.

The resting plate 3 is divided in the position to be placed under a knee (at the hollow of the knee) to bend the resting, plate 3 in such a way that a bent leg at the knee joint will still rest with all its parts on the resting plate 3. Thereby the resting plate 3, preferably consisting of two subsections 3a, 3b is construed in such away that it does not damage or harm the hollow of the knee by e.g., having a foldable, flexible sheet placed over the joint of the two subsections. The resting plate 3 is raised either manually or by using a motor operating on a screw means raising said subsections. On either side of the resting plate 3 a number of holes 4 are arranged in parallel with the extension of the resting plate 3. This holes 4 are arranged to receive a pole 5 to which a straining band 6 can be attached. By applying the straining band to a knee, the knee and leg can be flexed sidewise and be held in such a position during CT or MRT attaching the band to the said pole.

A foot plate 7 is part of the device according to invention as well. The foot plate 7 comprises a support for a foot, whereby the support is supported in two different points 8,9. Hereby the upper part of the support is provided with a journal running in a track or groove and being arranged to be locked in a central position. The lower part of the support is in the same way provided with a journal running in a track or groove and likewise arranged to be locked in a central position. Both journals are arranged to be either locked simultaneously, or one be locked and the other fee in its tack or groove. The tracks or grooves allow the support to be turned sidewise up to 30° from a vertical line in the centre, i.e., in total 60° from side to side. This is due for both the upper as well as the lower parts. This means that a foot placed upon the support can be rotated sidewise to the left or the right from a forward directed position either around the heel or around the matrix. The foot support is hereby preferably provided with a stop to prevent the foot from going back into a normal position.

Further the foot plate 7 is arranged to slide along a track 10 in the resting plate 3 in order to have the foot plate 7 follow the foot when, and if, the knee is raised to a bent position. Thereby the foot plate 7 is arranged to be locked in a position allowing a normal resting of the foot onto the foot plate 7 when the knee has been raised.

The adjustment of the position of the foot plate 7 can be made either manually or by means of a motor operating to move the foot plate 7 to and fro. Care should be taken not to interfere with the CT or MRT if a motor should be installed.

Further, the foot plate 7 is arranged to adopt the raising of the knee in such a way that the foot angle visavi the leg remains in a normal position, i.e., about 90° between leg and foot. In case, however, the ligament controlling the bending forward of a foot should be examined, there is a further possibility to turn the foot plate 7 around a horizontal axis 11 as well. To this effect there is a further pivot attached horizontally at the middle of the foot plate 7 around which the foot plate 7 can be turned to effect such an adjustment.

Between the foot plate 7 and the waist arrangement there are at least two pulling cords 12 or strings arranged, whereby each string individually can be disconnected/connected to the foot plate 7/waist arrangements. Each string comprises a tension meter 13 and a straining means 14 arranged in such a way that each string can be stretched individually, whereby the tension in each string can be monitored. The staining means can, in a simple embodiment, be a mechanical rolling device, manually or motor driven. The tension meters are preferably of an electronic type so that they can be attached to a computer for collecting data necessary to determine and document the conditions used.

The patient provided with the device of the invention is placed upon a resting surface of a patient table being suitable for being introduced in a device for computed tomography or magnetic resonance tomography. Computed tomography and magnetic resonance tomography are known units and are subject of the present invention.

By having at least four cords or strings the different bending conditions can be achieved. During normal examination the tension in the cords will be about 25 to 50 kpm, whereby under certain extreme conditions it may be as high as 50 to 100 kpm or even higher, e.g. when studying a damage, where the ankle, knee and hip joints have been subject to very high forces and loads. The number of cords can be increased if more specific bending conditions will be achieved. In such cases four, six or even eight cords or strings with their respective tension meters can be attached.

The tension meters 13 may also be connected to a motor which affects the straining of the cords whereby a predetermined, adjusted value can be maintained as the tension meters control the motor.

At an examination a patient is placed on his back on the resting surface of the patient table of a tomography apparatus the waist arrangement is arranged around the hip region and the knee and foot plate 7 arrangements are arranged to the of the patient, whereby the knee bend determines the position of the foot plate 7 along the resting plate 3, whereafter the cords or strings 12 with their respective tension meters 13 are attached between'the two arrangements (waist and foot plate 7). The cords or strings are strained to a predetermined value, and the patient is brought into the tomography apparatus to obtain the pictures wanted. To determine conditions using a magnetic resonance tomograph certain special accessories (such as flex coils) can be needed to obtain the right signals due to a distance between the signal receiving parts and the patient. However, this is common knowledge to the operator of such tomographs, and is not part of the invention.

An alternative to the tension meters 13 is a meter 13a sensing the force by which the foot presses upon the foot plate 7.

What is claimed is:

1. Device for compression of the lower extremities for medical imaging purposes, in particular for diagnostic purposes at complementary examination using computed tomography (CT) or magnetic resonance tomography (MAT)

characterized in
that the device comprises
a waist arrangement (1) to be placed around and in first contact with the hip region of a patient,
a knee arrangement (2) to be placed in the vicinity of and in film contact with the knee of a patient,
a foot plate (7) comprising pressure sensors (13, 13a) and being arranged to accommodate a foot or the feet of a patient, whereby said sensors (13, 13a) are arranged to monitor the pressure of the respective foot on said foot plate (7),
strings (12) connecting said waist arrangement (1) and said foot plate (7) arrangement, which strings (12) can be stretched independently of each other and comprise each a tension meter (13) to monitor the force by which the strings (12) are strained.

2. Device according to claim 1,
characterized in that the straining force of the strings (5) is arranged to be regulated manually.

3. Device according to claim 1,
characterized in that the straining force of the strings (5) is arranged to be regulated using a motor.

4. Device according to claim 1,
characterized in that the straining force of the strings (5) is arranged to be regulated using a motor controlled by said tension meters (6).

5. Device according to claim 1,
characterized in that the knee arrangement is arranged to facilitate a bending of a knee as well as a twisting thereof, at different bending degrees.

6. Device according to claim 1,
characterized in that the foot plate (7) is arranged to be adopted to the bending of the knee with regard to its longitudinal position visavi the patient's body, as well as the angle between foot and foot plate (7).

* * * * *